United States Patent [19]

Wandell

[11] Patent Number: Plant 6,993

[45] Date of Patent: Aug. 22, 1989

[54] RED MAPLE NAMED WANDELL

[76] Inventor: Willet N. Wandell, Rte. #1, Box 286, Oquawka, Ill. 61469

[21] Appl. No.: 157,944

[22] Filed: Feb. 19, 1988

[51] Int. Cl.[4] ..... A01H 5/00

[52] U.S. Cl. ..... Plt./51

[58] Field of Search ..... Plt./51

[56] References Cited

PUBLICATIONS

Elias, T. S. (1980) "Red Maple" *Trees of North America* Publisher: Book Division Times Mirror Magazines, Inc., 380 Madison Ave., N.Y., N.Y. 10017, pp. 783–785.

*Primary Examiner*—James R. Feyrer

[57] ABSTRACT

A new variety of *Acer rubrum* of attractive, pyramidal growth habit, medium size, and early, uniform brilliant scarlet fall coloration. The tree has a full, dense and heavily leaved crown.

5 Drawing Sheets

This new variety of red maple was discovered by me growing in a nursery row of seedlings at Wandell's Nursery of Urbana, Ill. in 1969. I currently have 125 trees of this selection propagated by chip budding in my nursery at Oquawka, Ill., all of which maintain the distinguishing characteristics of the parent tree.

SUMMARY OF INVENTION

A new and distinct variety of red maple characterized by its brilliant scarlet fall color, the leaves turning color in the fall uniformly, evenly and earlier than other red maples; leaves produced abundantly in the canopy; stout petioles firmly hold the leaves so that the visual impact of fall color is enhanced, even under windy conditions. A unique pattern of branch development, the branches and twigs ascending at first, then arching downward, than once again ascending forming a graceful appearance and fully displaying the leaves; a pyramidal growth habit rather than the common globose crown of other red maples; leaf emergence that occurs later in the spring than other observed red maples, preventing late spring frost damage; and the limbs of young trees exhibit the ability to grow into and fill open gaps in the crown, presenting a full and dense tree crown with a high leaf population.

BRIEF DESCRIPTION OF THE DRAWINGS

FIG. 1 is a photographic view of the tree in leaf and showing the dense, full canopy highly populated with leaves and the pyramidal growth shape of the crown.

FIG. 2 is a photographic view of the distinct pattern of branch development, first ascending, then gracefully arching downward and outward, then once again ascending and producing a compact full canopy tree with a dense crown.

FIG. 3 is a photographic view of the leaves and showing the smaller than typical size and the unique upright carriage on the stout petioles.

FIG. 4 is a photographic view of the tree and showing the uniform scarlet fall color well presented by the flat carriage of the leaves by the petioles.

FIG. 5 is a photographic view of the bark of the tree.

FIG. 6 is a drawing of the dormant bud showing the leaf scars.

DESCRIPTION OF THE NEW PLANT

The following is a detailed description of my new cultivar with color designations according to The R.H.S. Colour Chart published by The Royal Horticultural Society of London, England and the stated observations having been made at Urbane, Ill. by applicant.

Origin: Seedling growing under cultivated conditons.

Parentage: A tree of unknown origin and parentage found growing in 1969.

Propagation: Maintains its distinguishing characteristics when asexually propagated by budding and grown-on under nursery conditions.

Classification: *Acer rubrum* var. 'Wandell'.

Form: Medium-sized tree.

Habit: Deciduous tree with a single trunk and a straight, single leader; crown pyramidal in shape, maintaining a neat, symmetrical appearance, dense with many leaves produced within the canopy; branches ascending and then arching outward and downward. Typical crotch angle branches emerge from the bole at a 45 degree angle dipping to a 60 degree angle and then each branch later returns as terminal growth develop.

Growth rate: Moderate.

Bark: Medium gray, mostly smooth with horizontal rings or bands when young, becoming longitudinally fissured.

Leaves: Oppositely arranged, deciduous, simple; blades palmately 3-lobed, 6–8.5 cm long and 3.5–7 cm wide, broadest above the middle, green (R.H.S. 137A) above, a paler (R.H.S. 191C) below, turning brilliant scarlet (R.H.S. 53A) in autumn, beginning in late September glabrous above and below except for a few hairs in the axils of basal veins on the lower surface, the tips acuminate, the margins doubly serrate, the bases rounded-truncate; petioles stout, holding the leaves flat, 3.5–7 cm long, reddish.

Winter buds: 3–4 mm long, rounded, dark red, with about 4 exposed, blunt, ciliate scales, often with numerous flower buds forming whorled clusters at the apical nodes.

Twigs: Moderately stout, 2–4 mm in diameter, ascending when young but soon becoming somewhat deflexed, glabrous, reddish-brown, marked with slightly raised ellipsoidal lenticels, lacking a strong foetid odor when crushed. Leaf scars opposite, connected by a fine line, v-shaped, very fine, stipule scars lacking.

Flowers: Only male flowers observed on subject tree, produced in multiple flowered clusters; yellow flowers are born on separate stalks produced in pendulant multiple flowered clusters 10 to 13 cm long. Individual flowers have a short 5 lobed calyx into inconspicuous petals and 5 to 8 stamens.

Seeds: None observed.

I claim:

1. A new and distinct variety *Acer rubrum* named 'Wandell' as described and illustrated herein that differs from all other varieties by the unique combination of (1) brilliant scarlet fall color; (2) leaves all turning color at the same time in the fall; (3) leaves turning color earlier in the fall than other red maples, not affected by early fall frosts; (4) leaves that are smaller than the species; (5) abundant leaf population within the canopy; (6) petioles that are stout, holding the leaves flat and upright so that the visual impact of fall color is enhanced, even in windy conditions; (7) branches and twigs ascending at first, then arching downward, forming a graceful appearance and fully displaying the leaves; (8) a pyramidal growth habit; (9) later leaf emergence in the spring than other red maples, not affected by late spring frosts; and (10) the limbs of young trees are able to grow into and fill in gaps in the crown so that more branches and higher leaf populations are accommodated.

* * * * *

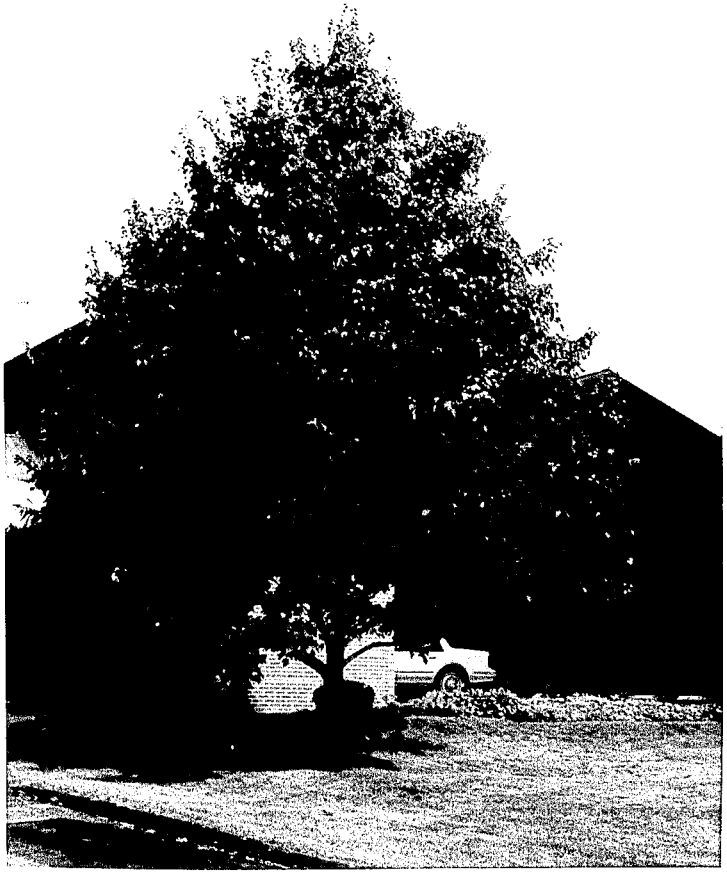
FIG. #1

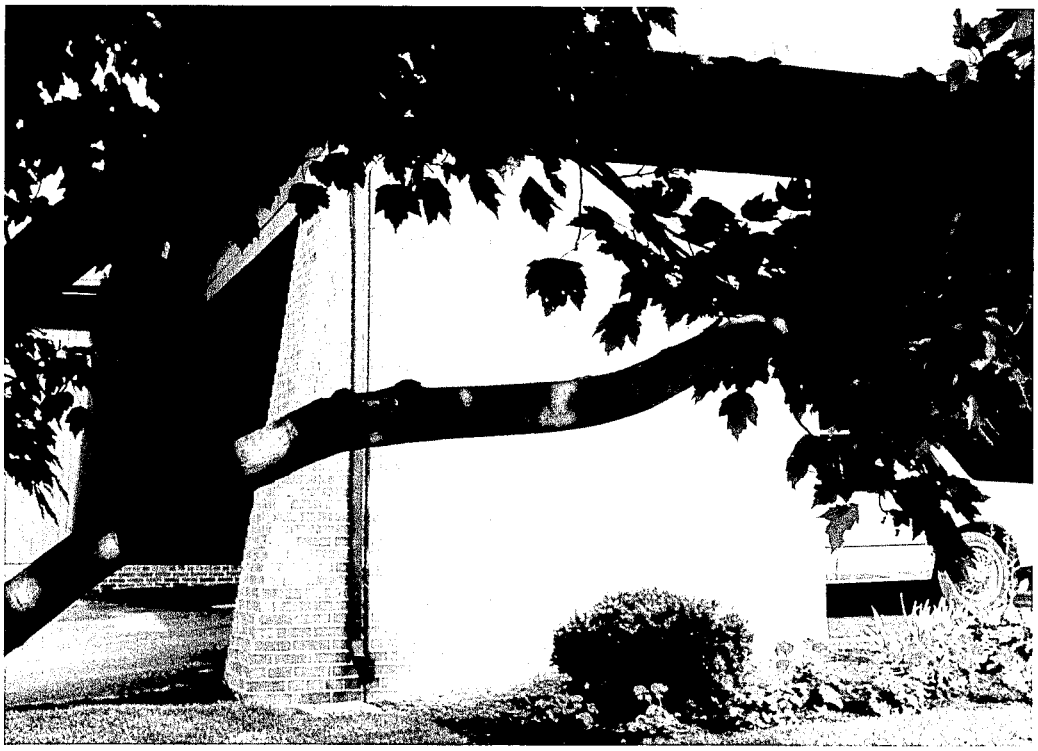
FIG. #2
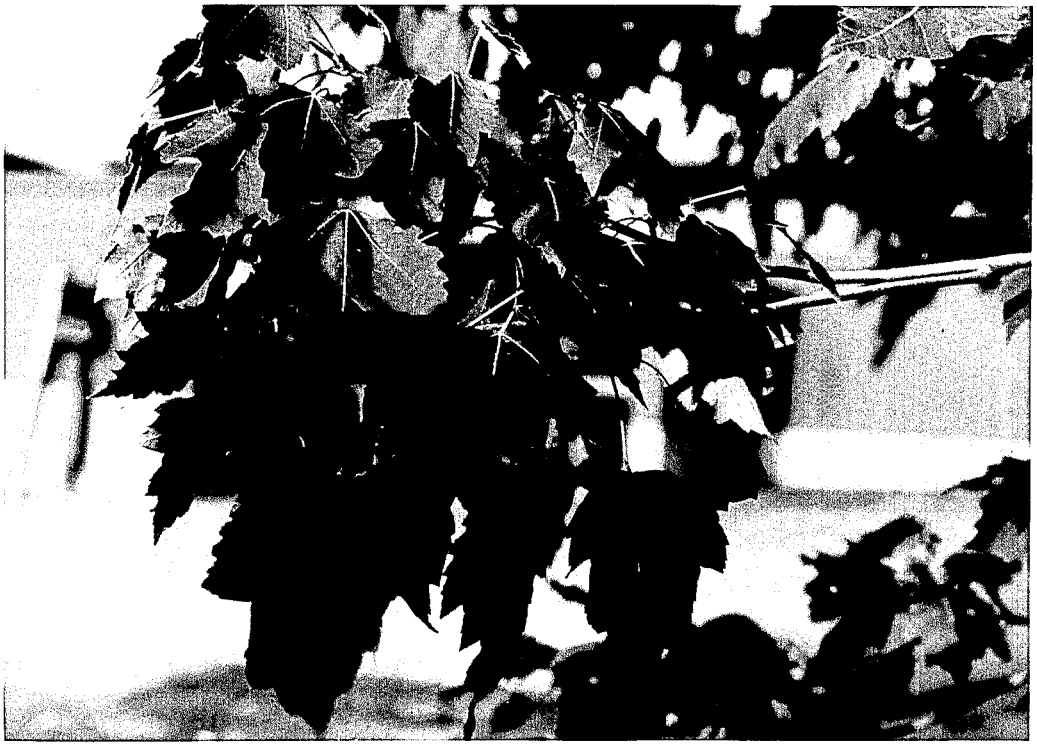
FIG. #3

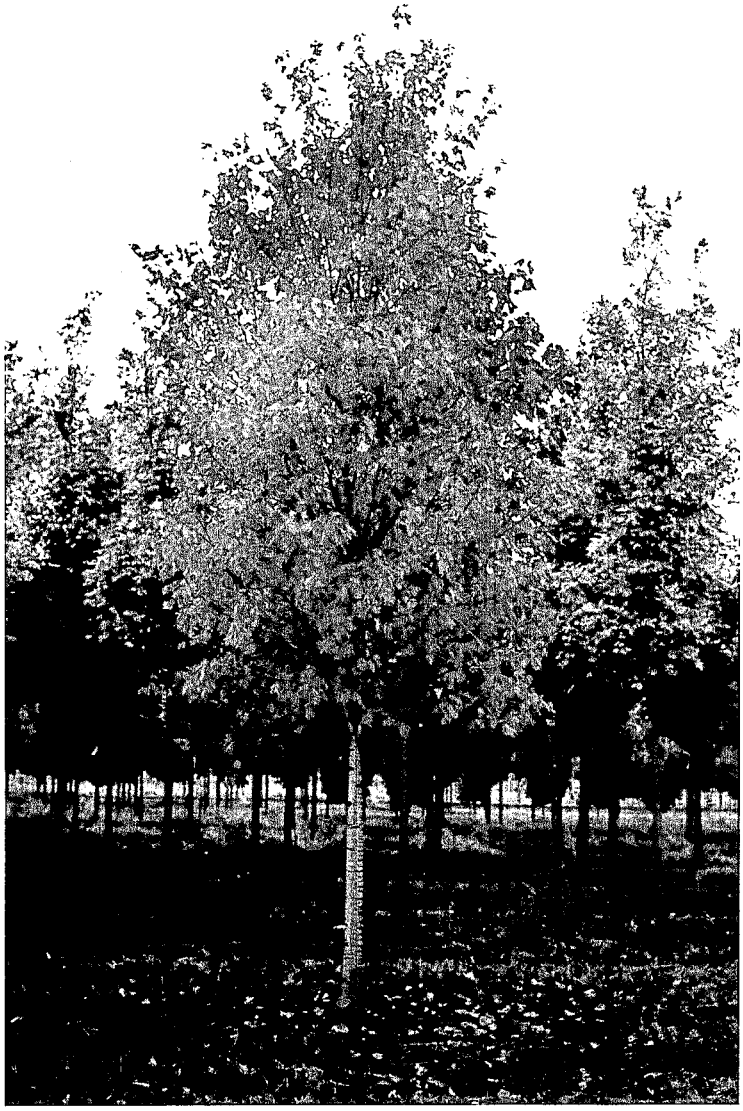
FIG. #4

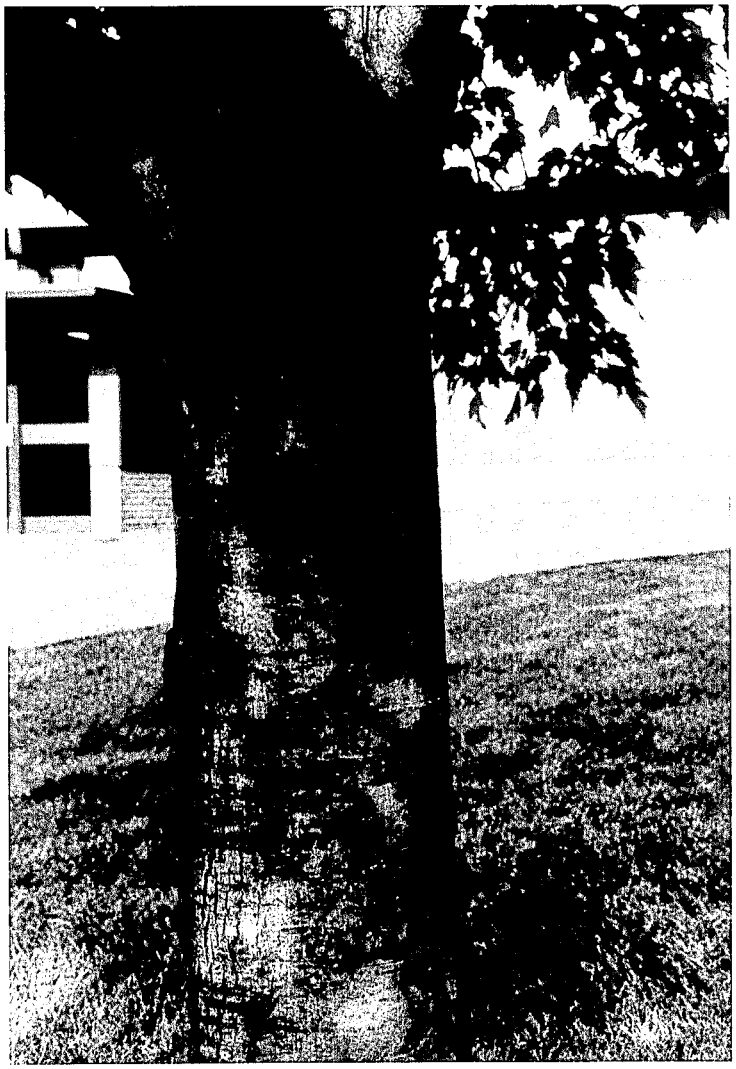
FIG. #5

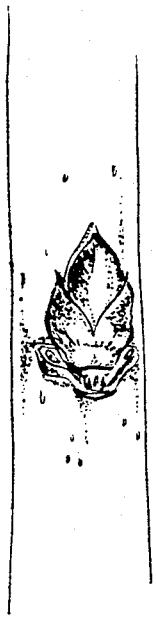
Fig. #6